(12) United States Patent
Bolton

(10) Patent No.: US 6,669,965 B2
(45) Date of Patent: *Dec. 30, 2003

(54) METHOD OF TREATING ATHEROSCLEROSIS

(75) Inventor: Anthony E. Bolton, Tideswell (CA)

(73) Assignee: Vasogen Ireland Limited, County Clare (IE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/436,243

(22) Filed: Nov. 9, 1999

(65) Prior Publication Data

US 2002/0086064 A1 Jul. 4, 2002

Related U.S. Application Data

(63) Continuation-in-part of application No. 08/754,348, filed on Nov. 22, 1996, now Pat. No. 5,980,954, which is a continuation-in-part of application No. 08/352,802, filed on Dec. 1, 1994, now Pat. No. 5,591,457, which is a continuation-in-part of application No. 07/941,327, filed on Sep. 4, 1992, now abandoned, which is a continuation-in-part of application No. 07/832,798, filed on Feb. 7, 1992, now abandoned.

(51) Int. Cl.$^7$ .......................... A61K 33/00; A61K 35/14

(52) U.S. Cl. ................... 424/613; 424/93.7; 424/93.71; 424/529; 424/534; 514/824; 604/4.01; 604/6.08

(58) Field of Search .................. 250/493.1; 422/24, 422/44, 45, 46; 424/613, 810, 93.7, 93.71, 529, 534; 514/824, 929; 435/2, 372, 375, 377; 604/4, 4.01, 6.08

(56) References Cited

U.S. PATENT DOCUMENTS

| | | | |
|---|---|---|---|
| 695,657 A | 3/1902 | Smith ........................ 604/25 |
| 3,715,430 A | 2/1973 | Ryan ........................ 424/613 |
| 3,925,344 A | 12/1975 | Mazur ........................ 530/385 |
| 4,061,736 A | 12/1977 | Morris et al. ................ 514/6 |
| 4,473,496 A | 9/1984 | Scannon ...................... 530/385 |
| 4,500,534 A | 2/1985 | Frehel et al. ................ 514/301 |
| 4,529,719 A | 7/1985 | Tye .............................. 514/6 |
| 4,584,130 A | 4/1986 | Bucci et al. ................ 530/385 |
| 4,600,531 A | 7/1986 | Walder ........................ 530/385 |
| 4,632,980 A | 12/1986 | Zee et al. .................... 530/380 |
| 4,659,726 A | 4/1987 | Yoshino et al. .............. 514/365 |
| 4,826,811 A | 5/1989 | Sehgal et al. ................. 514/6 |
| 4,831,268 A | 5/1989 | Fisch et al. ............. 250/432 R |
| 4,857,636 A | 8/1989 | Hsia .......................... 530/385 |
| 4,968,483 A | 11/1990 | Müller et al. ................ 422/45 |
| 4,983,637 A | 1/1991 | Herman ...................... 514/724 |
| 5,028,588 A | 7/1991 | Hoffman et al. .............. 514/6 |
| 5,052,382 A | 10/1991 | Wainwright .......... 128/202.25 |
| 5,194,590 A | 3/1993 | Sehgal et al. ................ 530/385 |
| 5,250,665 A | 10/1993 | Kluger et al. ................ 530/385 |
| 5,591,457 A | 1/1997 | Bolton ........................ 424/613 |
| 5,834,030 A | 11/1998 | Bolton ........................ 424/613 |
| 5,980,954 A | * 11/1999 | Bolton ........................ 424/613 |
| 6,264,646 B1 | * 7/2001 | Stewart ...................... 604/522 |

FOREIGN PATENT DOCUMENTS

| | | |
|---|---|---|
| DE | 1068428 | 5/1957 |
| DE | 2926523 | 1/1981 |
| EP | 0 111 418 A | 6/1984 |
| EP | 0 284 409 A | 9/1988 |
| JP | 58198466 | 2/1984 |
| WO | WO 92 10198 A | 6/1992 |
| WO | 93/15778 | 8/1993 |
| WO | WO 96/34613 | 11/1996 |
| WO | 98/07436 | 2/1998 |

OTHER PUBLICATIONS

Caulada–Benedetti, Z., et al. "Comparison of Th1–and Th2–Associated Immune Reactivites Stimulated by Single Versus Multiple Vaccination of Mice with Irradiated Schistosoma mansoni Cercariae." *J. Immunol.* 146(5): 1655–1660 (1991).

Chemical Abstracts. 100: 99189m (1984).

Murina, M.A., et al. "Changes in erythrocyte and thrombocyte aggregation after ultraviolet irradiation." *Biofizika.* 29(1): 92–95 (1984). (Summary in English).

*Physician's Guide to Rare Diseases.* Thoene, et al. (eds.) Dowden Publishing Co., NJ. 787–790 (1992).

Edelson, "Photopheresis: a Clinically Relevant Immunobiologic Response Modifier," *Annals of the New York Academy of Sciences*, Jan., 1991, pp 154–164, vol. 636.

Knobler et al., "Parenteral administration of 8–methoxypsoralen in photopheresis," *J. Am. Acad. Dermatol.*, 1993, pp. 580–584, vol. 28, No. 4.

Rook et al., "Extracorporeal photochemotherapy in the treatment of cutaneous T cell lymphoma and autoimmune disorders affecting the skin," *Ciba Foundation Symposium*, 1989, pp. 171–177, vol. 146.

Harrison's Principles of Internal Medicine (1994, 13th Ed.), pp. 1106–1116.*

(List continued on next page.)

*Primary Examiner*—Jose' G. Dees
*Assistant Examiner*—Frank Choi
(74) *Attorney, Agent, or Firm*—Burns, Doane, Swecker & Mathis LLP

(57) ABSTRACT

A method of treating or preventing atherosclerosis in a mammalian subject comprises: (a) extracting the aliquot of blood from the subject; (b) treating the aliquot of blood ex vivo with at least one stressor selected from the group consisting of an oxidizing agent, ultraviolet radiation and elevated temperature; and (c) administering the aliquot of blood treated in step (b) to the subject. Preferably, the aliquot has a volume of from about 0.01 ml to about 400 ml and is treated simultaneously by ozone gas and ultraviolet radiation at a temperature of from 37–55° C.

9 Claims, 5 Drawing Sheets

(4 of 5 Drawing Sheet(s) Filed in Color)

OTHER PUBLICATIONS

Harrison's Principles of Internal Medicine (1980, 9th Ed.), pp. 1156–1166.*

Medline Abstract 91104111, abstracting: Petukhov, E.B. et al, "Correction of Blood Hyperviscosity . . . " Grud Seroechnososudistaia Khir, (1990) (10), pp. 34–37.

Medline Abstract 90020932, abstracting: Petukhov, E.B. et al. "Decreased Activity of Lipid . . . ", Vestn Khir (May 1989), vol. 142(5), pp. 36–39.

Medline Abstract 80130497, abstracting: Vella Briffa D. et al. "Inhibition of human blood platelet aggregation . . . " Br. J. Dermatol. (Dec. 1979), vol. 101(6), pp. 679–683.

Drug Facts and Comparisons, 1994 edition, published by Facts and Comparisons, St. Louis, see pp. 263–269.

Cecil Textbook of Medicine, 19$^{th}$ ed., published by W.B. Saunders Co., PA, 1992, pp. 253–269, 823, 1085, 1530–1534 and 2161.

Physicians' Desk Reference, 47$^{th}$ ed., published by Medical Economics Data, NJ, 1993, pp. 710 and 2408–2411.

Rook, Alain H. et al., "Treatment of Autoimmune Disease with Extracorporeal Photochemotherapy: progressive systemic sclerosis," The Yale J. of Biology and Medicine, vol. 62, No. 6, Nov./Dec. 1989, pp. 639–645.

Tattoni, G. et al., "Osservazioni sull'efficacia di un trattamento balneoterapico ozonizzato in pazienti affetti da vasculopatie periferiche," Minerva Cardioangiologica, vol. 25/9, 1997, pp. 745–748.

"Cloned and Expressed Nitric Oxide Synthase Structurally Resembles Cytochrome P–450 Reductase," Nature, Jun. 27, 1992, vol. 351, pp. 714–718.

British Medical Journal, vol. 296, Jan. 30, 1988, pp. 320–331, entitled "Secondary Prevention of Vascular Disease by Prolonged Antiplatelet Treatment".

"Ozone: Historical Review," published in Biomedical Technology, Dec. 16, 1991, p. 5.

"Biological Roles of Nitric Oxide," Scientific American, May 1992, pp. 68–77.

D. Baran et al (associates) "Technical Report and Clinical Update" Mueller Medical International Inc., Oakville, Ontario, Canada, Sep. 1990.

Harbrecht, B.G., "Nitric Oxide Sysntesis Serves to Reduce Hepatic Damage During Acute Murine Endotoxemia." *Critical Care Med.* 20(11): 1568–1574 (1992).

Hishikawa, K., et al. "Effect of systemic L–arginine administration on hemodynamics and nitric oxide release in man." *Jap. Heart Jrnl.* 33(1): 41–48 (1992).

Thomsen, L.L., et al. "Tumor–Dependent Increased Plasma Nitrate Concentrations as an Indication of the Antitumor Effect of Flavone–8–Acetic Acid and Analogues in Mice," *Cancer Research.* 51(1): 77–81 (1991).

* cited by examiner

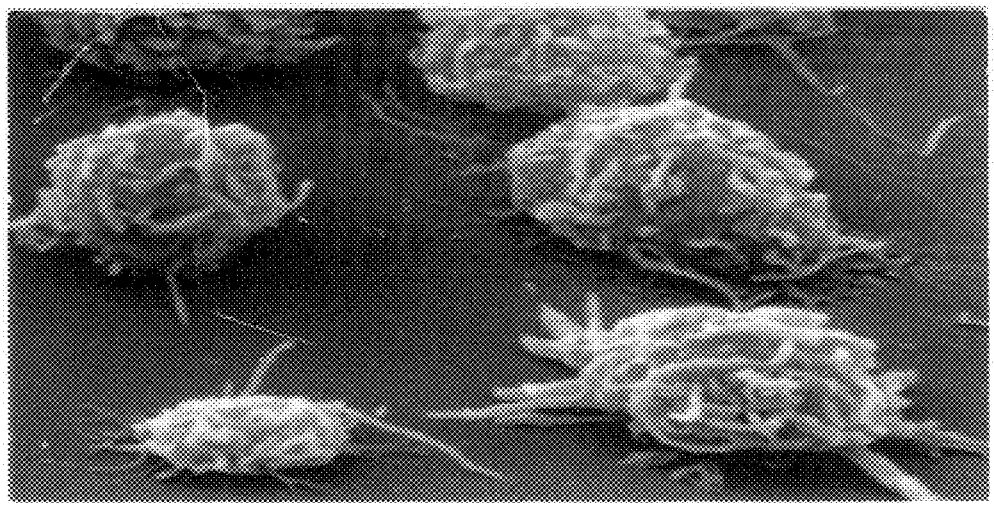
FIG._1A
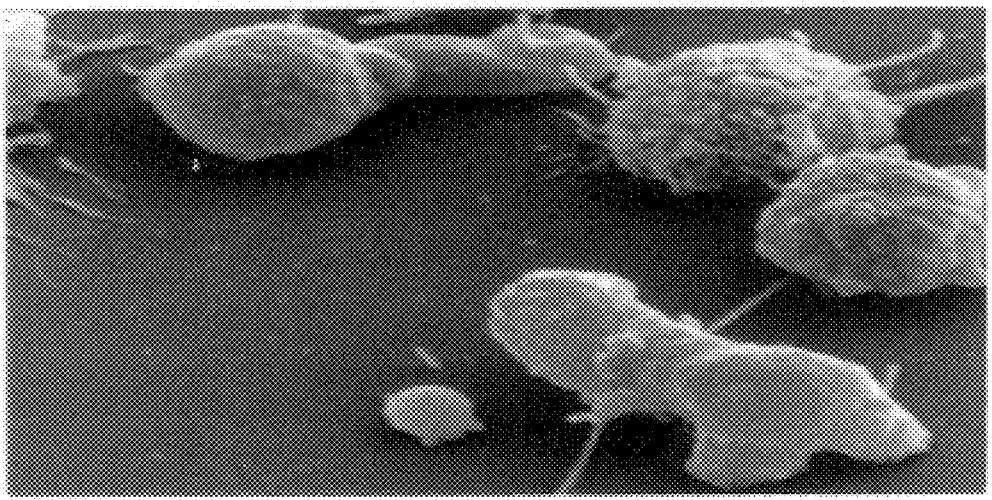
FIG._1B

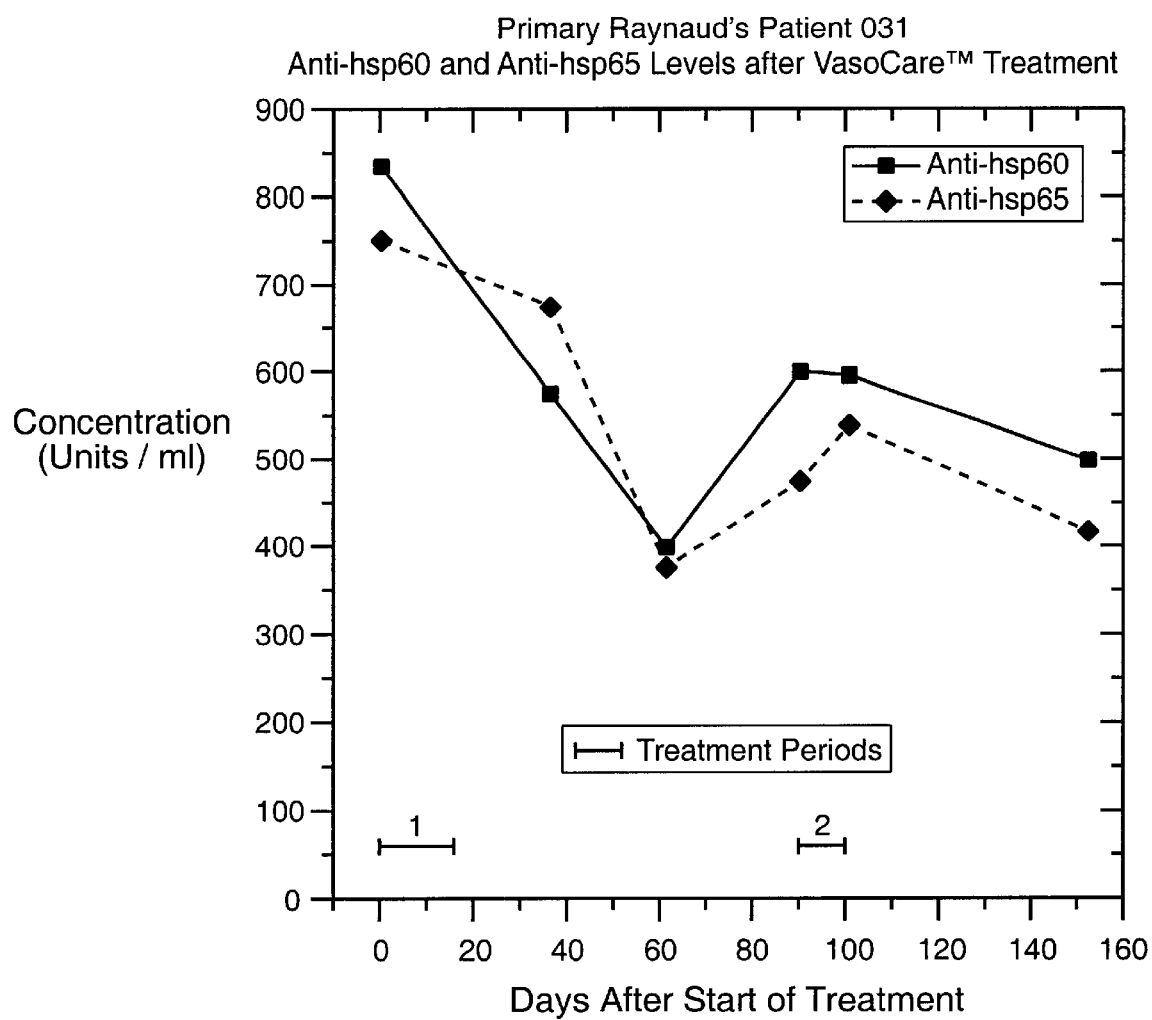
FIG._2

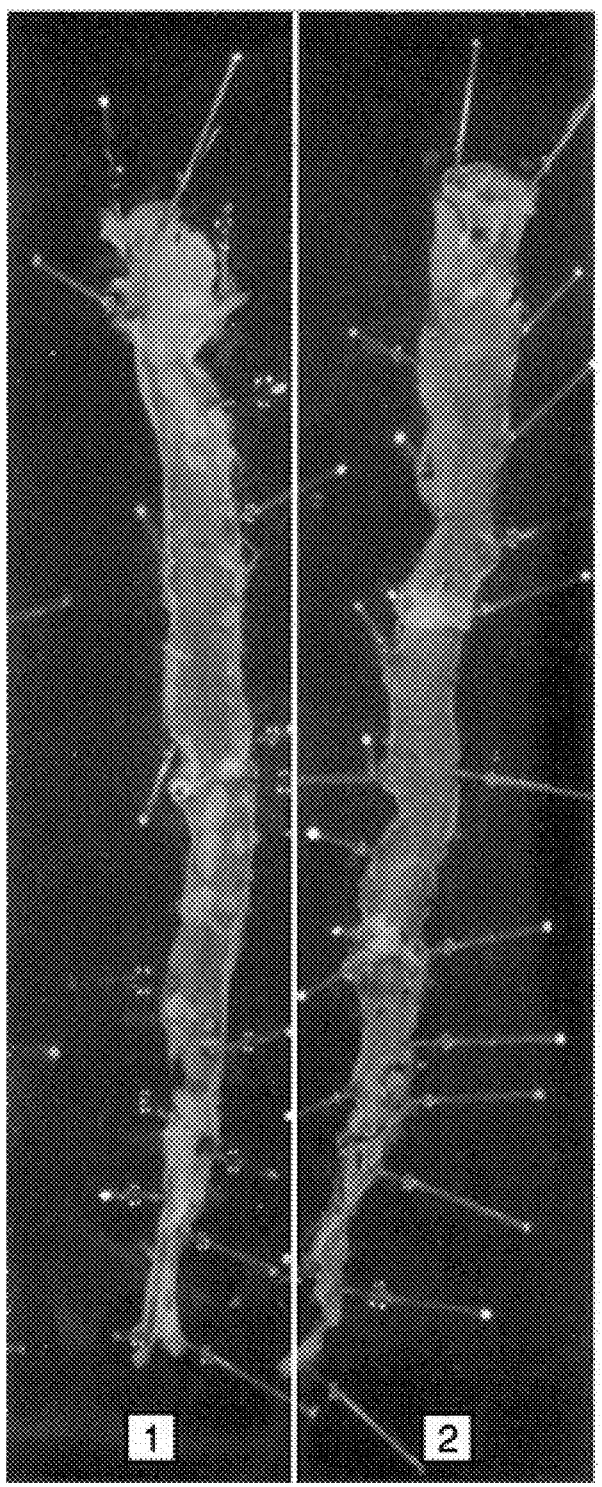
*FIG._3A   FIG._3B*

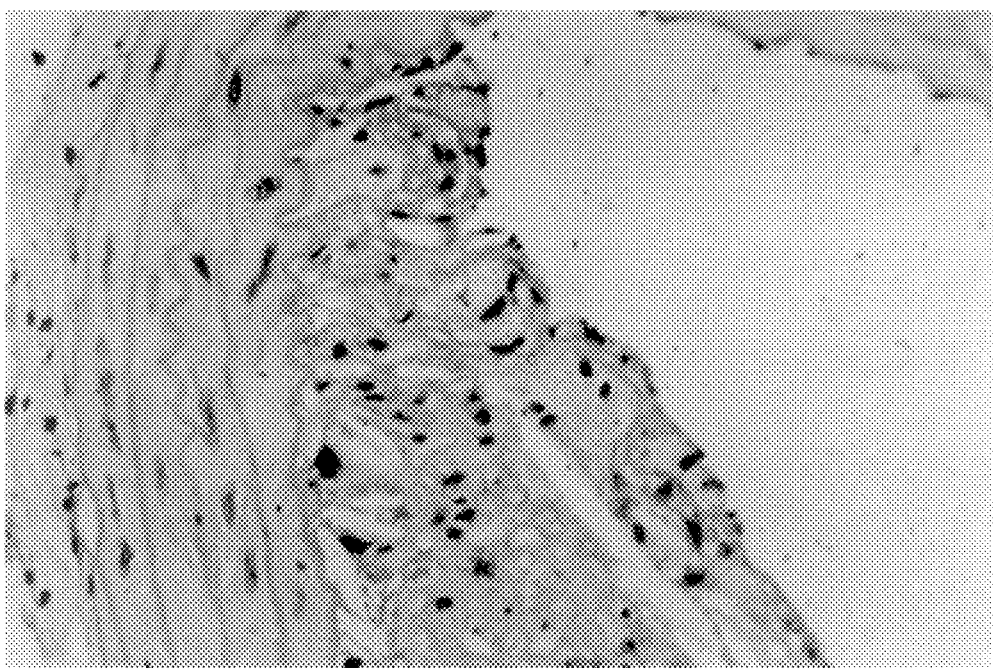
FIG._4
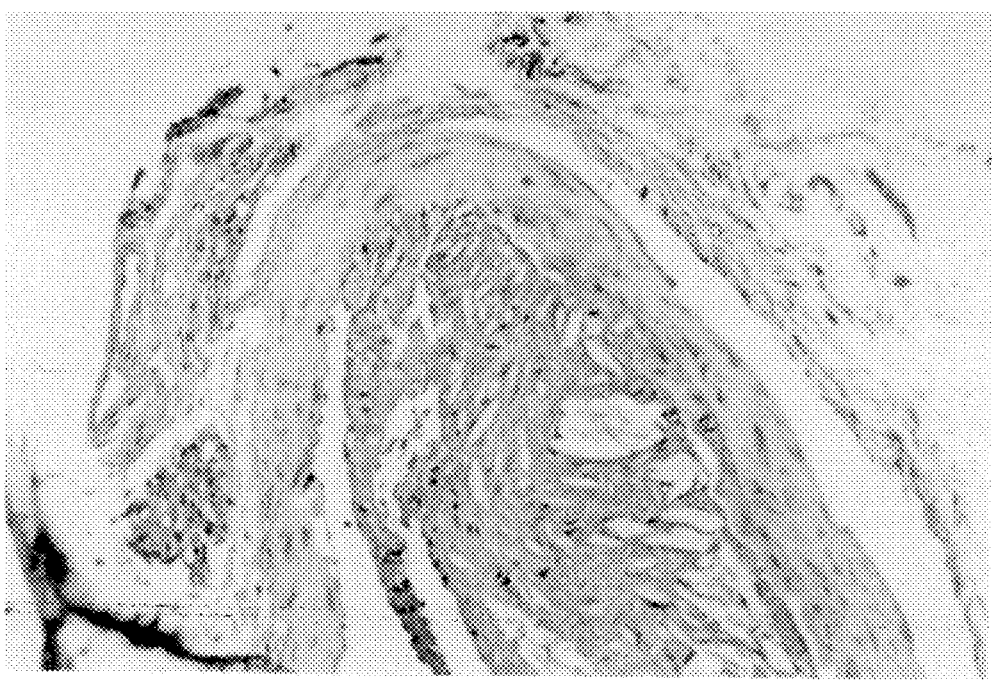
FIG._5

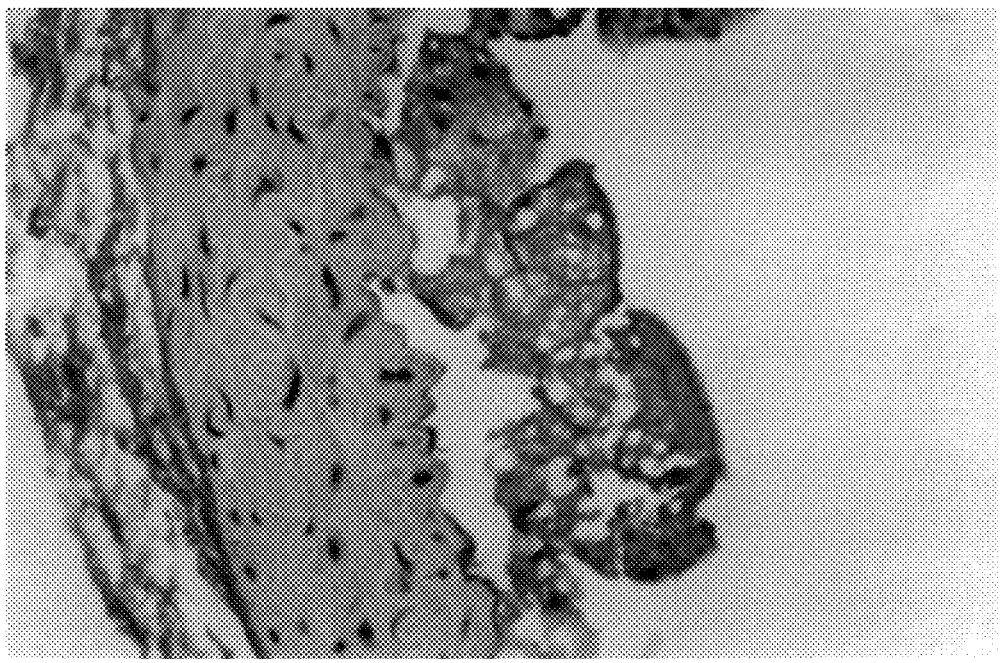
FIG._6

METHOD OF TREATING ATHEROSCLEROSIS

CROSS-REFERENCE TO RELATED APPLICATIONS

This application is a continuation-in-part of U.S. patent application Ser. No. 08/754,348, filed Nov. 22, 1996 which is issued Nov. 9, 1999 as U.S. Pat. No. 5,980,954 which is a continuation-in-part of U.S. patent application Ser. No. 08/352,802 filed Dec. 1, 1994 and which issued on Jan. 7, 1997 as U.S. Pat. No. 5,591,457, which is in turn a continuation-in-part of U.S. patent application Ser. No. 07/941,327 filed Sep. 4, 1992 and now abandoned, which was in turn a continuation-in-part of U.S. patent application Ser. No. 07/832,798 (now abandoned) filed Feb. 7, 1992.

FIELD OF THE INVENTION

This invention relates to vaccines, their preparation and use in medical treatments. More particularly, it relates to treatments for alleviating autoimmune diseases and their symptoms, to a vaccine useful therein, and to processes for preparing and using such a vaccine. In one particularly preferred aspect, the present invention relates to methods for treating and preventing atherosclerosis.

BACKGROUND OF THE INVENTION

Autoimmune (immune-mediated) diseases include rheumatoid arthritis, graft versus host disease, systemic lupus erythromatosis (SLE), scleroderma, multiple sclerosis, diabetes, organ rejection, inflammatory bowel disease, psoriasis, and other afflictions. It is becoming increasingly apparent that many vascular disorders, including atherosclerotic forms of such disorders, have an autoimmune component, and a number of patients with vascular disease have circulating auto antibodies. Autoimmune diseases may be divided into two general types, namely systemic autoimmune diseases (exemplified by arthritis, lupus and scleroderma), and organ-specific (exemplified by multiple sclerosis, diabetes and atherosclerosis, in which latter case the vasculature is regarded as a specific organ).

In general terms, a normally functioning immune system distinguishes between the antigens of foreign invading organisms (non-self) and tissues native to its own body (self), so as to provide a defence against foreign organisms. Central to the proper functioning of the immune system, therefore, is the ability of the system to discriminate between self and non-self. When a patient's immune system fails to discriminate between self and non-self and starts to react against self antigens, then an autoimmune disorder may arise.

The causes responsible for the reaction of an affected person's immune system against self are not fully understood, and several different theories have been put forward. The immune response to an antigen is triggered by the interaction of the antigen with receptors of predetermined specificity on certain lymphocytes. It is believed that, at an early stage in development of the immune system, those lymphocytes with receptors recognizing self antigens are recognized and eliminated from the body's system by a process of deletion. Alternatively, or in addition, such self-reactive lymphocytes may be controlled by the suppression of their activities. Both mechanisms probably occur.

The immune system of normal healthy individuals is able to identify and to react against a family of proteins which are highly conserved in nature (i.e. they have a similar structure throughout all living organisms). This family of proteins is called the stress or heat-shock proteins (HSP), and they are grouped according to their approximate molecular weights. Members of the HSP family include the HSP60 group, including, among others, proteins in the molecular weight range 50 to 100 kilodaltons. Increased production of HSP's was first identified as a response to heat stress, but this now appears to be part of a general response to a variety of cell stresses. HSPs are normally located within cells, and their function appears to be stabilization of the structure of various proteins in stressed cells, so as to protect the cell from the protein denaturing effects of various stressors. However, it is likely that HSPs have a number of other functions which are, as yet, not fully understood. Heat shock proteins, HSP's are discussed in some detail by William J. Welch, in an article in "Scientific American", May, 1993, page 56.

One group of the family of HSP's, the HSP60 group, contains proteins which show about 50% identity between bacterial cells and human cells. Infections with bacteria containing HSP 65 results in an immune response in healthy humans against the bacterial HSP65, evidenced by the production of anti-HSP65 antibodies. Thus, a healthy immune system appears to be able to identify and react against self-like antigens.

In certain pathologies, for example many autoimmune diseases such as rheumatoid arthritis and scleroderma, patients also show the presence of antibodies to HSP65. In the past, this has led to conclusions that autoimmune diseases result from bacterial infection. Now it seems likely that autoimmune diseases are associated with an inappropriate control of autoimmune response. In other words, it is possible that the antibodies to HSP65 result from an autoimmune reaction initiated by HSPs from the body itself, but one which has been improperly controlled. In such cases, therefore, it should be possible to control an inappropriate autoimmune response, by stimulating the body's natural immune control mechanisms, using a particularly and specific method of vaccination.

To stimulate the body's immune response, a vaccine is required which will, upon injection into the host body, enable the host immune system to present the antigens contained in the vaccine to cells of the host immune system. Antigen presentation is performed by antigen presenting cells.

A vaccine to treat autoimmune diseases should contain antigens or fragments thereof (peptides) that will activate the body's immune control mechanisms present. In addition, the antigens (peptides) should be present in a form which can be recognized by the host immune system when the vaccine is introduced into the host. Certain of the antigens may be present on intact cells. The objective of such a vaccination is to activate regulatory immune pathways, particularly those controlling autoimmune responses, thereby downregulating the autoimmune response.

The particular antigens which will activate the control mechanisms of a mammalian autoimmune system are not fully understood. It is however recognized that they may include antigens derived from lymphocyte receptors, which may function to stimulate control mechanisms, to inhibit those lymphocytes which cause pathological autoimmune responses in the patient. They may also include HSPs, such as the HSP60 group of proteins, and leucocyte surface molecules such as those of the Major Histocompatibility Complex (MHC) including MHC Class II molecules. MHC Class II molecules function physiologically to present peptides to $CD4^+$T-cells as part of the immune response.

It is important that the lymphocyte receptors and other cell-derived molecules for vaccination of an autoimmune suffering patient be derived from cells obtained from the same patient, since this system will contain the autoimmune specificity. Receptors on other leucocytes in the blood may alternatively or additionally be important in a proposed vaccination process. The use of such a system as the basis of a vaccine may be considered analogous to the use of a particular viral antigen as a vaccine to treat and prevent disease caused by that virus. A vaccine for treating an autoimmune disease should, therefore, be prepared from a sample of the patient's own blood. Such a vaccine may be described as an autovaccine.

For antigens to be effective in stimulating (or inhibiting) the immune system, the antigens should be presented to immune cells of the host system by antigen-presenting cells, which are naturally present in the body. Many of the antigen-presenting cells are phagocytes, which attach to the antigens, engulf them by phagocytosis, and break them down or process them. The preparation of such an autovaccine should include a process whereby the lymphocytes and other leucocytes in the vaccine, which may be a source of antigens, are modified into a form whereby they are likely to be phagocytosed by phagocytic antigen-presenting cells upon re-injection into the patient, so that the antigens or effective residues thereof are presented on the surface of an antigen-presenting cell. Then they can effect a controlling mechanism on the immune system, either inhibitory or stimulatory.

During the normal growth period of a mammalian body, tissues become reshaped with areas of cells being removed. This is accomplished by the cells' undergoing a process called programmed cell death or apoptosis, the apoptotic cells being phagocytosed while not becoming disrupted sufficient to expose self-antigens to the immune system.

BRIEF REFERENCE TO THE PRIOR ART

U.S. Pat. No. 3,715,430 Ryan relates to a method and apparatus for producing substantially pure oxygen having a controlled content of ozone and higher oxygen polymers. The purified oxygen gas is exposed to ultraviolet light in a wavelength of 2485 to 2537 angstrom units in order to produce 5 to 500 parts per million of ozone and higher oxygen polymers in the gas mixture. Ryan indicates that the gas produced in this manner is non-irritating to the human body and may be intravenously injected into the blood stream for therapeutic use.

U.S. Pat. No. 4,632,980 Zee et al. discloses a method of freeing blood and blood components of enveloped viruses by contacting the blood or blood product in an aqueous medium with an enveloped virus inactivating amount of ozone. The treatment is carried out at a temperature of 4° to 37° C., and an ozone concentration of 1–100 ppm.

U.S. Pat. No. 4,831,268 Fisch et al. provides a method for the radiation of blood to prevent arteriosclerosis related heart and vascular diseases caused by disturbances in the fat exchange. The disclosed process involves irradiating the blood in a blood conducting tube with radiation having an intensity of from about 1 mWcm$^{-2}$ to 10 mWcm$^{-2}$ in a wavelength range of from about 300 to 600 nm.

U.S. Pat. No. 4,968,483 Müller et al. describes an apparatus for oxygenating blood, by treating an aliquot of a patient's blood, extracorporeally, with an oxygen/ozone mixture and ultraviolet light, at a controlled temperature. The apparatus is proposed for use in haematological oxidation therapy.

U.S. Pat. No. 5,052,382 Wainwright discloses an apparatus for the controlled generation and administration of ozone. The apparatus includes a generator for generating ozone, a monitor for monitoring the ozone production, a dosage device for providing a predetermined amount of ozone administration, and a computer control device for controlling the operation of the apparatus. The patent further discloses that administration of ozone to patients is known for the treatment of viral and bacterial infections, as well as for the treatment of external sores and wounds.

SUMMARY OF THE INVENTION

It is an object of the present invention to provide a novel autovaccine useful in the prevention and alleviation of symptoms of atherosclerosis.

It is a further object of the present invention to provide a novel process for the preparation of such an autovaccine.

It is a further and more specific object of the present invention to provide a novel method for prevention and alleviation of the symptoms of atherosclerosis in a mammalian subject, preferably a human subject.

Accordingly, the present invention provides, from a first aspect, an autovaccine for prevention and treatment of atherosclerosis in a mammalian subject, and derived from an aliquot of the subject's own blood. The autovaccine is characterized by the presence therein, in comparison with the normal blood of the patient, of at least one of the following characterizing features:

increasing numbers of lymphocytes and other leucocytes, exhibiting a condensed apoptotic-like morphology;

a release of specific proteins from the cell surface of the blood leucocytes, including the MHC Class II molecule HLA-DR, resulting in a reduction in the number of cells expressing such surface proteins;

an upregulation in the expression of certain cell surface markers for example CD-11a, a component of the ligand for the cell adhesion molecule ICAM-1; and certain T-cell regulatory molecules;

an increase in the amount of heat shock protein HSP-60 in the plasma;

a decrease in HSP-72 within the lymphocytes.

By inducing an apoptotic-like state in the lymphocytes and other leucocytes in the blood comprising the autovaccine, as evidenced by the increased numbers of lymphocytes and other leucocytes exhibiting a condensed apoptotic-like morphology therein, these cells may become more readily phagocytosed upon re-injection into the host body.

There are a number of different phagocytic cell types present in the mammalian body, including various antigen presenting cells and neutrophils. In order to facilitate phagocytosis by antigen presenting cells rather than by other phagocytes, the lymphocytes and other leucocytes present in the autovaccine of the invention are treated so that they may interact preferentially with antigen presenting phagocytic cells. Cells adhere to each other by a number of mechanisms including the expression of cell adhesion molecules. Cell adhesion molecules present on one cell type interact with specific ligand for particular adhesion molecules present on the adhering cell type. The present invention may result in a preferential interaction of cells in the autovaccine to antigen presenting cells in the host body, by upregulation, on the surface of the cells in the autovaccine, of the expression of the ligand for adhesion molecules found on antigen-presenting cells in the host body. Antigen-presenting cells express a number of cell adhesion molecules, including ICAM-1, a component of the ligand of which is CD-11a. One way by which the process of the invention may change the preferential phagocytosis of apoptosing cells is by upregulation of CD-11a.

The preparation of the autovaccine according to the present invention comprises extracting from the subject an aliquot of blood of volume about 0.01 ml to about 400 ml, and contacting the aliquot of blood, extracorporeally, with an immune system-stimulating effective amount of ozone gas and ultraviolet radiation.

The method for preventing and alleviating the symptoms of atherosclerosis in a human subject, in accordance with the present invention, comprises extracting from the patient an aliquot of blood of volume about 0.001 ml to about 400 ml, contacting the aliquot of blood, extracorporeally, with an immune system-stimulating amount of ozone gas and ultraviolet radiation, followed by administering the treated blood aliquot to the subject.

In another aspect, the present invention provides a method of treating or preventing atherosclerosis in a mammalian subject, comprising: (a) extracting an aliquot of blood from the subject; (b) treating the aliquot of blood ex vivo with at least one stressor selected from the group consisting of an oxidizing agent, ultraviolet radiation and elevated temperature; and (c) administering the aliquot of blood treated in step (b) to the subject.

BRIEF DESCRIPTION OF THE DRAWINGS

The patent file contains at least one drawing executed in color. Copies of this patent with the color drawing(s) will be provided by the Office upon request and payment of the necessary fee.

The accompanying drawing

FIG. 1 shows scanning electron micrographs of peripheral blood mononuclear cells isolated from whole blood by density gradient centrifugation, the micrograph labeled (A) showing mononuclear cells obtained from an untreated blood sample, and the micrograph labeled (B) showing mononuclear cells obtained from a sample of blood treated according to the method of the present invention;

FIG. 2 is a graphical presentation of the results of Example 2 below;

FIG. 3 comprises photographs of two full length aortae obtained from LDL receptor deficient mice which underwent the study described in Example 5, the aorta labeled 1 being obtained from an animal which received a high cholesterol diet and sham treatments, and the aorta labeled 2 being obtained from an animal which received a high cholesterol diet and was treated according to a preferred method of the present invention, with aortic lipid deposition being made visible by staining the aortae with oil red O; and FIGS. 4 to 6 comprise photographs of aortic cross-sections obtained from LDL receptor deficient mice which underwent the study described in Example 5, the aorta shown in FIG. 4 being obtained from an animal which received a normal diet, the aorta of FIG. 5 being obtained from an animal which received the high cholesterol diet and sham treatments, and the aorta of FIG. 6 being obtained from an animal which received a high cholesterol diet and was treated according to a preferred method of the present invention, with the presence of macrophages in the aortic plaque deposits being made visible by immunostaining the aortae.

DESCRIPTION OF THE PREFERRED EMBODIMENTS

When the autovaccine according to the present invention is injected into the autoimmune patient, significant alleviation of the patient's autoimmune condition is experienced, as set out in the specific embodiments of the invention described below. Exactly how the vaccine operates following this re-injection is not currently fully understood. The following tentative explanations are offered for a better and more complete description of the invention, but are not to be considered as binding or limiting.

T-cells, which are one kind of lymphocyte and which play a significant role in the control of the immune system, include CD-8 cells, and CD-4 cells otherwise known as T-helper cells, further subdividable into TH1 and TH2 cells. The TH1 cells secrete pro-inflammatory cytokines such as interferon gamma. The TH2 cells are considered to be regulatory cells and secrete regulatory cytokines, such as interleukin-4. In a normal, healthy individual, the ratio of TH1 cells to TH2 cells is around 3:1. In autoimmune conditions, there is usually an imbalance in the TH cell types, often with an increase in the TH1 cells compared to the TH2 cells, i.e. there is a change in the ratio between them, with a consequent development of an inflammatory condition often noted in autoimmune disease. A number of components of the autovaccine of the present invention, possibly including HLA-DR and/or other MHC antigens released from the leucocyte cell surfaces, upregulate the TH2 cells in the patient's blood and/or locally at the site of the inflammation, thereby increasing the secretion of regulatory cytokines, and/or upregulating the suppressor cells to stimulate an inhibitory pathway for the autoimmune disease and alleviate or even switch off the autoimmune response pathway.

It is also commonly accepted that autoimmune disease sufferers may have significant populations of abnormal autoreactive T-cells, which are partly responsible for the autoimmune disease. The autoimmune disease suffering patient's ability to suppress these autoreactive T-cells is compromised. The autovaccine of the invention restores the system towards a normal immune state.

The autovaccine is prepared by exposing the blood aliquot to at least one stressor, in controlled amounts, the stressor being selected from among oxidizing agents such as ozone, ultraviolet radiation and elevated temperature, and combinations of two or more of such stressors. The resulting blood aliquot, after such treatment, serves as an autovaccine, and can be reinjected into the autoimmune patient. Following a course of such treatments, a patients signs and symptoms of autoimmune disease such as those of rheumatoid arthritis, scleroderma and the like are markedly reduced. The subjective reports of alleviation of symptoms of rheumatoid arthritis are consistent with objective measurements of relative erythrocyte sedimentation rates, an objective test accepted as meaningful in measuring the progression of an autoimmune disease such as rheumatoid arthritis, by the American College of Rheumatology.

In preparing the autovaccine according to the invention, by modification of a blood aliquot extracted from the patient, the blood cells are stressed. This affects the heat shock proteins, HSP, contained in the cell. HSP-60 levels in the mononuclear cells are reduced, and are increased in the plasma. Further, the level of HSP-72 present in the mononuclear cells is reduced. Also as a result of the process of the invention, certain surface (membrane) proteins on the lymphocytes, for example HLA-DR, are reduced whereas others, such as CD-3, do not change and yet others such as CD-11a in neutrophils are upregulated. Accordingly it is apparently not a non-specific membrane change which is occurring, nor is it cell destruction. It is a complex active process.

On microscopic visualization of the autovaccine according to the present invention, mononuclear cells with a condensed apoptotic-like morphology can be observed, suggesting the presence in the autovaccine of increased numbers of apoptosing cells capable of preferential phagocytosis upon reinjection, for appropriate presentation of the antigens of the autoimmune disease. The effect of the treatment of the present invention on the morphology of blood mononuclear cells is illustrated in FIG. 1, which shows scanning electron micrographs of (A) mononuclear cells from untreated blood and (B) mononuclear cells from blood treated according to the method of the invention. The blood cells were isolated from whole blood by density gradient centrifugation and observed under scanning electron microscopy.

In the preferred autovaccine in accordance with the present invention, the number of mononuclear cells or leucocytes exhibiting the presence of HSP-60 therein is decreased, as does the amount of HSP-60 in each cell, as compared with the normal, untreated peripheral blood of the source patient. Whereas the patient normally has, typically, about 30% of mononuclear cells exhibiting the presence of NSP-60 therein (as measured by whole blood intracellular flow cytometry), the autovaccine has only 12–20%. In clinical studies, it has been found that the figure reduces from 29.3% to 15.5%, mean of six tests. Preferably also, the number of leucocytes exhibiting the presence of HSP-72, which is about 50% in the untreated blood of the source patient, is reduced to 25–35% in the autovaccine of the present invention. In clinical studies, this figure for HSP-72 reduced from 49.4% in untreated blood to 30.2% in the autovaccine, mean of six tests, similarly measured.

The number of cells which express the cell surface specific protein HLA-DR, in the preferred autovaccine of the present invention, is reduced as compared with the patient's untreated blood, possibly as a result of its release from the cell surface. Typically, the number of cells expressing HLA-DR reduces from about 23% to about 8–12%, as measured by whole blood flow cytometry. In clinical studies, this figure reduced from 23.3% to 10.3%, mean of five experiments.

The upregulation of the surface marker CD-11a in the preferred autovaccine of the present invention can be expressed as an increase in the percentage of neutrophils in the autovaccine which test positive for CD-11a, compared with the patient's source blood. Typically, the increase is from about 10% up to the approximate range 70–95%. In clinical studies, an increase from 10.3% to 84% was obtained, mean of six tests.

A significant feature of the present invention is that the source of the blood from which the autovaccine is prepared for a specific patient suffering from an autoimmune disease is the patient himself or herself. The antigens forming the basis of the autovaccine find their origin in the patient's own blood. No extraneous antigens are added; the effective antigens are present in the patient's blood, and/or are released or modified by the process of preparing the autovaccine using the patient's own blood as the source material. Moreover, in many cases, the precise autoimmune disease from which the patient suffers appears to be immaterial. The antigens for the autovaccine for the disease are present in, or are developed by treatment of, the patient's own blood.

Preferably, the stressors to which the leucocytes in the extracted blood aliquot are subjected are a temperature stress (blood temperature above body temperature), an oxidative environment, such as a mixture of ozone and oxygen bubbled through the blood aliquot, and ultraviolet radiation, simultaneously or successively, but preferably simultaneously.

The present invention provides a method of preventing and alleviating the symptoms of an autoimmune disease in a human, specifically atherosclerosis, which comprises:

(a) contacting of about 0.01 ml to about 400 ml of blood with an immune system modifying effective amount of ozone gas and ultraviolet radiation; and (b) administering the blood treated in step (a) to a human.

In another aspect, the present invention provides a method of treating or preventing atherosclerosis in a mammalian subject, comprising: (a) extracting an aliquot of blood from the subject; (b) treating the aliquot of blood ex vivo with at least one stressor selected from the group consisting of an oxidizing agent, ultraviolet radiation and elevated temperature; and (c) administering the aliquot of blood treated in step (b) to the subject.

In general, from about 0.01 ml to about 400 ml of blood may be treated according to the invention. Preferred amounts are in the range of about 0.1 ml to 200 ml. More suitably, the aliquot for treatment has a volume of from about 0.1–100 mls, preferably 1–50 ml and most preferably 5–15 mls. The method most preferably involves treating an aliquot of about 10 mls of blood with ozone gas and ultraviolet radiation, then re-administering the treated blood to the patient by intramuscular injection.

As noted, it is preferred, according to the invention, to apply all three of the aforementioned stressors simultaneously to the aliquot under treatment. Care must be taken not to utilize an excessive level of the stressors, to the extent that the cell membranes of the white cells are caused to be disrupted.

The temperature stressor must keep the aliquot in the liquid phase, i.e. from about 0° C. to about 56° C. and should not heat it above about 55° C. Any suitable source of heat known in the art may be employed to heat the blood, preferably one or more infrared lamps. Preferably the temperature stressor warms the aliquot being treated, to a temperature above normal body temperature, i.e. to about 37–55° C., and most preferably from about 37–43° C., e.g. about 42.5° C. Preferably the temperature of the blood aliquot is maintained at this elevated temperature during the treatment with UV/ozone.

Alternatively, the blood sample is heated while being subjected to UV radiation, until the blood reaches a predetermined temperature (preferably about 42.5° C.), at which point bubbling of ozone gas through the blood is commenced. The concurrent UV/ozone treatment is then maintained for a predetermined period of time, preferably about 3 minutes.

Another alternative method involved subjecting the blood to UV/ozone while heating to a predetermined temperature (preferably about 42.5° C.), then either ending the treatment once the predetermined temperature is reached, or continuing UV/ozone treatment for a further period of time, most preferably about 3 minutes.

The application of the oxidative stressor preferably involves exposing the aliquot to a mixture of medical grade oxygen and ozone gas, most preferably by bubbling through the aliquot, at the aforementioned temperature range, a stream of medical grade oxygen gas having ozone as a minor component therein. The ozone gas may be provided by any conventional source known in the art. Suitably the gas stream has an ozone content of from 0.5–100 $\mu$g/ml, or about 1.0–100 $\mu$g/ml, preferably 3–70 $\mu$g/ml, and most preferably from about 5–50 $\mu$g/ml. The gas stream is supplied to the aliquot at a rate of from about 0.01–2.0 liters per minute, preferably 0.1–1.0 liters per minute and most preferably at about 0.12 liters per minute (STP).

The ultraviolet radiation stressor is suitably applied by irradiating the aliquot under treatment from an appropriate source of UV radiation, while the aliquot is maintained at the aforementioned temperature and while the oxygen/ozone gaseous mixture is being bubbled through the aliquot. The ultraviolet radiation may be provided by any conventional source known in the art, for example by a plurality of low-pressure ultraviolet lamps. The method of the invention preferably utilizes a standard UV-C source of ultraviolet radiation, namely UV lamps emitting in the C-band wavelengths, i.e. at wavelengths shorter than about 280 mn. Ultraviolet radiation corresponding to standard UV-A and UV-B sources can also be used. Preferably employed are low-pressure ultraviolet lamps that generate a line spectrum wherein at least 90% of the radiation has a wavelength of about 253.7 nm. An appropriate dosage of such UV radiation, applied simultaneously with the aforementioned temperature and oxidative environment stressors, is obtained from lamps with a power output of from about 15 to about 25 watts, at the chosen UV wavelength, arranged to surround the sample container holding the aliquot, each lamp providing an intensity, at a distance of 1 meter, of from about 45–65 mW/sq.cm. Several such lamps surrounding the sample bottle, with a combined output at 253.7 nm of 15–25 watts, operated at maximum intensity, may advantageously be used. At the incident surface of the blood, the UV energy supplied is 0.2–0.25 Joules per $cm^2$. Such a treatment provides a blood aliquot which is appropriately modified according to the invention to create the autovaccine outlined above ready for re-injection into the patient.

The time for which the aliquot is subjected to the stressors can be from a few seconds to about 60 minutes. It is normally within the time range of from about 0.5–60 minutes. This depends to some extent upon the chosen intensity of the UV irradiation, the temperature and the concentration of the rate at which the oxidizing agent is supplied to the aliquot. The more severe the stressors applied to the aliquot, generally the shorter time for which they need to be applied. Some experimentation to establish optimum times may be necessary on the part of the operator, once the other stressor levels have been set. Under most stressor conditions, preferred times will be in the approximate range of about 0.5–10 minutes, most preferably 2–5 minutes, and normally around 3 minutes. The starting blood temperature, and the rate at which it can be warmed or cooled to a predetermined temperature, tends to vary from patient to patient.

In the practice of the preferred process of the present invention, the blood aliquot (or the separated cellular fractions of the blood, or mixtures of the separated cells, including platelets, these various leucocyte-containing combinations, along with whole blood, being referred to collectively throughout as the "aliquot") may be treated with the stressors using an apparatus of the type described in U.S. Pat. No. 4,968,483 Mueller. The aliquot is placed in a suitable, sterile, UV-radiation-transmissive container, which is then fitted into the machine. The temperature of the aliquot is adjusted to the predetermined value, e.g. 42.5° C., by the use of a suitable heat source such as an IR lamp, and the UV lamps are switched on for a fixed period before the gas flow is applied to the aliquot providing the oxidative stress, to allow the output of the UV lamps to stabilize. Then the oxygen/ozone gas mixture, of known composition and controlled flow rate, is applied to the aliquot, for the predetermined duration of 0.5–60 minutes preferably 2–5 minutes and most preferably about 3 minutes as discussed above, so that the aliquot experiences all three stressors simultaneously. In this way, the blood aliquot is appropriately modified to produce an autovaccine according to the present invention sufficient to achieve the desired effects.

Example 4 below supports the finding that the method of treating blood according to the invention has an immune modifying effect. In particular, treatment of blood with UV/ozone has been found to increase the expression of activation markers on the surface of the lymphocytes.

Thus, the invention also provides a method of stimulating or activating the immune system in a human by contacting about 0.01 ml to about 400 ml of blood from a human with an immune system-stimulating effect amount of ozone gas and ultraviolet radiation, followed by administering the treated blood to a human. It is believed that this stimulation or activation of the immune system may have the effect of preventing and alleviating atherosclerosis. Similarly, the invention contemplates a method of treating an existing immune system disorder in a human, in particular atherosclerosis, by contacting about 0.01 ml to about 400 ml of blood from a human with an immune system-stimulating effective amount of ozone gas and ultraviolet radiation, followed by administering the treated blood to a human.

The immune system disorders which may be treated by this method include allergic conditions, autoimmune conditions, and inflammatory conditions. Specific immune system disorders which may be treated according to the invention include rheumatoid arthritis, scleroderma, diabetes mellitus, organ rejection, miscarriage, multiple sclerosis, inflammatory bowel disease, psoriasis, and other inflammatory disorders. The discoveries of the present invention may also be applied to treat autoimmune diseases which manifest as infertility, including endometriosis. It is also effective in treatment of atherosclerosis, which can be regarded as an autoimmune disease of the vasculature.

The invention is further described for illustrative purposes with reference to specific examples of pre-clinical and clinical use of it and objective and subjective results from such uses.

SPECIFIC DESCRIPTION OF THE MOST PREFERRED EMBODIMENTS

EXAMPLE 1

Thirty patients with active rheumatoid arthritis, 21 females and 9 males, were treated by the preferred process according to the present invention. The age range of the patients was 26–72 years, with the mean age 52.2 years, at the start of the study. Each patient received between 30 and 60 individual treatments (mean 48.3 treatments) over a time span of 62 weeks (mean 20.6 weeks). Each individual treatment consisted of the removal of 10 a mL aliquot of blood, the treatment of the blood aliquot simultaneously with gaseous oxygen/ozone mixture and ultraviolet light at elevated temperature using an apparatus as generally described in the aforementioned U.S. Pat. No. 4,968,483 Mueller et al.

The constitution of the gas mixture was 14–15 mcg/mL ozone/medical grade oxygen. The gas mixture was fed through the aliquot at a rate of about 200 mLs/minute, for a period of 3 minutes. The temperature of the aliquot was held steady at 42.5° C. The UV radiation has a wavelength of 253.7 nm.

Post treatment measurements were conducted 1 day to nine months after the final treatment of each patient (mean 12.4 weeks). Blood samples were taken and analyzed for leucocytes, erythrocyte sedimentation rate, rheumatoid factor and C-reactive protein, using standard test procedures. The erythrocyte sedimentation rate and C-reactive protein are elevated in most inflammatory conditions including rheumatoid arthritis, and Rheumatoid Factor is elevated in most cases of rheumatoid arthritis as well as in some cases of certain other autoimmune diseases. White blood cell count, erythrocyte sedimention rate, rheumatoid factor and C-reactive protein all showed significant reduction after the course of treatment. Particularly noteworthy is the significant reduction in erythrocyte sedimentation rate, an indicator of rheumatoid arthritis improvement, accepted by the American College of Rheumatology.

In addition, patients were rated by medical personnel subjectively, for the apparent severity of their rheumatoid arthritis symptoms, before and after the courses of treatment, on a scale of 5 (very bad) to 1 (excellent). Again, a marked improvement in each case was reported.

The mean results are given in Table 1 below.

TABLE 1

| Clinical Measurements | Normal Ranges | Pre-Treatment (Mean ± SD) | Post-Treatment (Mean ± SD) | Paired T-Test |
|---|---|---|---|---|
| Symptom Rating | | 3.9 ± 0.9 | 2.6 ± 0.6 | p<0.0001 |
| Leucocytes, $10^9$/L | 4.0–10.0 | 11.68 ± 2.81 | 8.70 ± 1.02 | p<0.0001 |
| Erythrocyte Sed. Rate 1 hr (mm) | 0–20 | 50.1 ± 22.9 | 28.1 ± 13.7 | p<0.0001 |
| Rheumatoid Factor iu | <100 | 117.0 ± 76.1 | 91.7 ± 67.4 | p<0.02 |
| C-Reactive Protein mg/L | <1.0 | 5.28 ± 3.62 | 3.73 ± 3.44 | p<0.009 |

EXAMPLE 2

Four patients with primary Raynaud's disease were given a course of therapy according to the invention, in an open clinical trial performed at St Bartholomew's Hospital, London, under properly controlled and supervised conditions. All four patients showed alleviation of their symptoms following treatment.

An investigation of an autoimmune component of the disease in these patients demonstrated high levels of auto-antibodies specific for HSP-60 and HSP-65 in one patient. The levels of these auto-antibodies in this patient are shown on FIG. 2, from which it can be seen that the levels decreased markedly following a course of therapy. The first course of treatment, indicated "1" on FIG. 2, consisted of 9 treatments carried out over 14 days. Furthermore, the levels of these auto-antibodies began to increase again some weeks later, and were again lowered following a second course of therapy. The second course of treatment, indicated "2" on FIG. 2, consisted of 5 treatments carried out over 10 days. These data suggest that therapy with blood treated according to the invention, i.e. the autovaccine described herein, may reduce an autoimmune response as evidenced by a reduction of auto-antibodies in a treated patient.

EXAMPLE 3

The helper T-lymphocyte subsets TH1 and TH2 have been measured in 13 normal control volunteers and in two patients suffering from the autoimmune disease scleroderma. The ratio of TH1:TH2 in the controls, as measured by intracellular cytokine flow cytometry, was found to be 3.029+/−0.639 (mean+/−standard deviation). The patients with scleroderma had TH1:TH2 ratios of 5.0 and 4.58 respectively, most likely, indicating an increase in the TH1 population relative to the TH2 population. In inflammatory pathologies such as many autoimmune diseases there is a relative increase in the TH1 cells; therefore it was to be expected that this ratio would be higher in these patients than in the healthy control individuals.

Following a course of therapy with blood treated according to the invention (i.e. the autovaccine described herein), the TH1:TH2 ratios in these patients was 3.29 and 3.13 respectively, i.e. the ratio had approached the normal range. These data suggest that therapy with blood treated according to the present invention may reduce an autoimmune response as evidenced by a relative increase in the TH2 cells.

EXAMPLE 4

Staining of Activation Markers

This example illustrates an experimental approach which indicates that treatment of blood with UV/ozone according to the invention has an immune-stimulatory effect on human blood, as evidenced by an increase in certain activation markers on the surface of the treated mononuclear cells.

Samples (20 ml) of peripheral blood were taken from individuals. Each sample was divided into two aliquots. The first aliquot was treated according to the inventive technique, as follows:

The 10 ml aliquot was treated in vivo for three minutes with ozone gas (variable ozone concentration of 5.50 μg/ml) and ultraviolet light (253.7 nm), at a temperature of 42.5° C. An apparatus similar to that disclosed in U.S. Pat. No. 4,968,483 was utilized to carry out the treatment of the blood sample.

The second 10 ml aliquot from each sample served as an untreated control.

Each blood sample was stained for certain activation markers of T-lymphocytes using conventional monoclonal antibody techniques. The proportion of the total cells which stained positive for the individual markers was quantitated by microscopy. The results are shown in Table 2 below.

TABLE 2

| Marker | Control | Ozone/UV Treated |
|---|---|---|
| CD25 (IL-2 receptor) | 1% | 26% |
| CD2 (E-rosette receptor) | 3% | 33% |

The above data for this example are all means of duplicates, and indicate that treatment with UV/ozone according to the invention results in the activation of T-lymphocytes.

EXAMPLE 5

Model

The purpose of the experiment is to determine the effects of treatment according the present invention on the development of atherosclerosis in the LDL receptor (LDL-R) deficient mouse model, a widely used transgenic atherosclerosis model created by targeted disruption of the LDL receptor. This animal model is analogous to familial hypercholesterolemia, an inherited condition in which a mutation results in complete lack of functional LDL-R. In the human disease, homozygous individuals demonstrate a marked increase in serum cholesterol and develop severe premature atherosclerosis, often succumbing to this disease at an early age. In patients with this disease, currently used lipid lowering agents do not have a significant effect in terms of lowering cholesterol levels.

The LDL-R deficient mouse model shows intolerance to cholesterol feeding and develops widespread atherosclerotic changes which progress to mature fibrous lesions morphologically indistinguishable from established human atherosclerosis. Apart from the defined genetic abnormality causing predisposition to atherosclerosis, this model has the advantage of rapid development of widespread atherosclerosis within 6 to 8 weeks following institution of cholesterol feeding.

Protocol

LDL-R deficient mice were purchased from Jackson Laboratories. A total of 20 mice were entered into the study at 22 weeks of age, and 15 mice completed the study. The length of the study was 8 weeks. The mice were maintained on a 12 hour dark/12 hour light cycle with free access to food and water, and were fed a specified diet as follows. A control group comprised of 5 animals, all of which completed the study, received a normal diet. The high cholesterol group comprising 15 animals, of which 10 completed the study, were fed a diet containing 1.25% cholesterol, 7.5% cocoa butter, 7.5% casein, and 0.5% sodium cholate. To ensure proper food intake, food consumption and animal weight were monitored on a weekly basis. In previous experiments, it was demonstrated that 8 weeks of feeding with the high cholesterol diet results in substantial atherosclerosis development, particularly in the aortic arch and the descending thoracic aorta.

Treatment

Ten of the animals fed the high cholesterol diet were selected at random to undergo a course of treatment by the preferred method of the invention. Six of the treated animals completed the study. It is to be noted that the four deaths in this group were not in any way related to the treatment, but occurred early in the study as a result of fighting among animals which were housed together during the study. The other five animals on the high cholesterol diet underwent a course of sham treatments, and four survived the protocol.

The treatments began four weeks after initiation of the study, with each of the animals on the high cholesterol diet receiving a total of 10 treatments (2 courses of treatment of 1 injection per day for 5 days, the 2 courses of treatment separated by two days, i.e. 10 injections over a period of 12 days). Each individual treatment administered to the animals treated by the method of the present invention consisted of the collection of 10 ml of blood from genetically compatible donor animals fed on a normal diet, the blood being collected into sodium citrate anticoagulant. In order to collect each 10 ml aliquot of blood, about 1 ml of blood was extracted from each of 10 animals. The blood was extracted by cardiac puncture, with the animals being under full xylazine/ketamine anesthesia during the blood extraction procedure, and being giver T-61 immediately following extraction. The blood aliquot was transferred to a sterile, disposable, low-density polyethylene vessel for ex vivo treatment, and was then treated simultaneously with a gaseous oxygen/ozone mixture and ultraviolet light at elevated temperature using an apparatus as generally described in aforementioned U.S. Pat. No. 4,968,483 to Mueller et al.

The constitution of the gas mixture was 14.5±1.0 $\mu$g ozone/ml, with the remainder of the mixture comprising medical grade oxygen. The gas mixture was bubbled through the aliquot at a rate of 240±24 ml/min for a period of 3 minutes. The temperature of the aliquot was held steady at 42.5±1.0 °C. The UV light was within the UV-C band, and included a wavelength of 253.7 nm.

After treatment by the preferred method of the present invention, 30 $\mu$l of the treated blood was re-injected intramuscularly into each animal undergoing treatment according to the present invention.

In the sham treatments, 30 $\mu$l of untreated blood was injected intramuscularly into each of the remaining five animals on the high cholesterol diet.

Assessment of Atherosclerosis

After 8 weeks, the animals were anesthetized with zylaxine/ketamine and the heart was exposed. After nicking the vena cava to obtain blood samples, the animals were perfused via ventricular puncture, first with PBS to flush out the blood and then with 10% neutral buffered formalin for 3 minutes to fix the aorta. The thoracic aorta was dissected away from the thorax en bloc and stored in 10% formalin at 4° C. Pressure-fixed (10% formalin) aortae were removed en bloc and opened to allow a longitudinal full length inversion. The aortae were then mounted internally exposed on glass slides and stained with oil red O. The bright red staining (indicating lipid deposition) was then quantified using a computer assisted morphometric system, and expressed as a percentage of total aortic intimal surface.

Plasma Lipid and Lipoprotein Analysis

Lipoprotein profiles were obtained by means of fast-phase liquid chromatography with a Superose 6B column. 200 $\mu$l aliquots of platelet-poor plasma from each animal were loaded onto the column and eluted with TSE buffer at a constant flow rate of 0.35 ml/min. An aliquot of 80 $\mu$l from each fraction was used for the measurement of total cholesterol minus eaterified cholesterol. Total cholesterol and triglycerides in plasma samples and column fractions for 11 representative animals were measured by an enzymatic method established in the lipid research group at St. Michael's Hospital, Toronto.

Statistical Analysis

Continuous variables are reported as mean±SD. Differences in cholesterol levels and triglyceride levels among groups were tested by student's t-test. Differences in atherosclerotic lesion area among groups were tested using the one-way ANOVA test in conjunction with the Bonferroni correction.

Results

FIG. 3 illustrates two full length aortae stained with oil red O to detect lipid deposition and plaque formation inside the arteries. The animals which received the high cholesterol diet and the sham treatments exhibited substantial aortic lipid deposition (aorta 1 in FIG. 3), with a ratio of atherosclerotic area (AA) to total area (TA) being 0.16±0.1. In comparison, those animals which were treated by the preferred method of the present invention showed a profoundly reduced level of aortic lipid deposition (aorta 2 in FIG. 3), with AA/TA being 0.04±0.02. These ratios are significantly different, with p<0.05. In the animals which received the normal diet, no significant atherosclerotic changes were observed.

In addition, the animals which were treated according to the preferred method of the present invention were observed to have better general appearance, reduced skin xanthomatosis (eyelids, nose and paws), reduced limb swelling, and better appetite than the untreated animals which received the high cholesterol diet.

To further illustrate the effects of the method of the present invention, sections of aortae obtained from animals in this example were immunostained for MOMA-2, a marker of inflammatory monocyte/macrophages. These results are illustrated in FIGS. 4 (normal diet), 5 (HC diet-no treatment) and 6 (HC diet-treated). No staining is seen in FIG. 4. Staining is visible in both FIGS. 5 and 6, indicating that the majority of cells in the neointima of the animals which received the high cholesterol diet were monocyte/macrophages. However, as seen by comparing FIGS. 5 and 6, animals that had been treated by the method of the invention showed a marked reduction in the amount of plaque deposition, and therefore also show a decrease in the overall number of monocyte/macrophages. This indicates a reduction in autoimmune/inflammatory processes in the plaque of treated compared to control animals.

The measurement of the cholesterol levels among the different groups of animals showed that the total serum cholesterol level did not change significantly in the animals which received the normal diet, but was markedly increased in the animals receiving the high cholesterol diet. This marked increase occurred both in the sham treated group and to a lesser extent in the group which received the treatments according to the preferred method of the present invention.

The measured triglyceride levels were also higher in the animals which received the high cholesterol diet, as compared to the animals which received the normal diet. However, among the animals which received the high cholesterol diet, the increase in triglyceride levels was much greater in the sham treated group than in the group which was treated according to the preferred method of the present invention.

The measured cholesterol and triglyceride levels, and the average cholesterol and triglyceride levels for each group, are shown below in Table 3.

TABLE 3

| GROUP | ANIMAL | CHOLESTEROL (mM) | TRIGYLCERIDES (mM) |
| --- | --- | --- | --- |
| Treated | 1 | 12.99 | 0.305 |
| Treated | 2 | 13.19 | 0.336 |
| Treated | 3 | 16.22 | 0.348 |
| Treated | 4 | 14.87 | 0.397 |
|  | Average (1–4) | 14.3 ± 1.5 | 0.35 ± 0.04 |
| Control | 6 | 4.41 | 0.341 |
| Control | 7 | 5.15 | 0.297 |
| Control | 8 | 5.73 | 0.440 |
|  | Average (6–8) | 5.1 ± 0.7 | 0.39 ± 0.05 |
| HC Diet | 11 | 27.52 | 0.697 |
| HC Diet | 12 | 26.59 | 0.720 |
| HC Diet | 13 | 23.45 | 0.605 |
| HC Diet | 14 | 24.56 | 0.636 |
|  | Average (11–14) | 25.5 ± 1.9 | 0.66 ± 0.05 |

In Table 3, the "Treated" group of animals received the high cholesterol diet and were treated according to the preferred method of the present invention, the "Control" animals received the normal diet and no treatment, and the "HC Diet" animals received the high cholesterol diet and the sham treatment.

EXAMPLE 6

In this study, LDL-R deficient mice were divided into groups and studied using the following protocol:
Group A (control)—fed a normal diet as in Example 5;
Group B1—fed a high cholesterol diet as described in Example 5 for 8 weeks;
Group B2—fed a high cholesterol diet as described in Example 5 for 12 weeks;
Group C1—fed a high cholesterol diet as described in Example 5 for 8 weeks, and treated by the preferred method of the present invention as described in Example 5 at 4 weeks of dietary intervention; and
Group C2—fed a high cholesterol diet as described in Example 5 for 12 weeks, and treated by the preferred method of the present invention as described in Example 5 at 8 weeks of dietary intervention.

For each group of animals, atherosclerotic area was assessed at either 8 or 12 weeks according to the method described in Example 5 under the heading "Assessment of Atherosclerosis". As demonstrated by measurement of atherosclerotic area, the animals of group B (high cholesterol diet alone) exhibited substantial aortic lipid deposition, with group B1 animals having levels of 0.16±0.1 at eight weeks and group B2 animals having levels of 0.17±0.1 at 12 weeks of dietary intervention. In contrast, the animals of group C (high cholesterol diet with treatment according to the invention) exhibited profoundly reduced lipid deposition, with group C1 animals having levels of 0.04±0.02 (p<0.05) at eight weeks of dietary intervention, and group C2 animals having levels of 0.04±0.02 (p<0.01) at twelve weeks of dietary intervention.

The animals of group C also exhibited a marked reduction in xanthelasma and limb swelling as compared to animals of group B.

Total lipoprotein profiles were measured as in Example 5 by fast-phase liquid chromatography and an enzyme-linked assay. The results of this analysis showed that the animals of group B (high cholesterol diet alone) had markedly increased levels of total serum cholesterol (CHO 46.71±3.61 mM) as compared to control group A (CHO 5.1±0.7 mM). The animals of group C did not show a significant reduction in cholesterol (CHO 44.69±2.83 mM; p=0.27 for B vs. C) as compared to the animals of group B.

As shown in above Examples 5 and 6, the treatment according to the present invention substantially inhibited the development of atherosclerosis in a mouse model of human familial hypercholesterolemia. In addition to substantially reducing the development of atherosclerosis at an early stage and inhibiting the progression of established atherosclerotic lesions, the treatment according to the preferred method of the present invention was shown to cause regression of existing atherosclerotic lesions. This can be seen for example by comparing the results for the animals of sub-groups B1 and C2 in Example 6, which show that existing plaque deposits at week eight of a high cholesterol diet are reduced by about 75% when the animals are treated at week eight according to the present invention. These improvements in cardiovascular health were accompanied by improvements in the animals' general overall appearance and appetite.

Furthermore, Example 5 indicates that the method of the invention also achieved about a forty percent reduction in total serum cholesterol and a significant reduction in triglyceride levels. However, Example 6 demonstrates that the retardation in progression and regression of atherosclerotic plaques is not necessarily accompanied by a significant reduction in serum lipid levels.

As discussed above, atherosclerosis has a significant immune-modulated inflammatory component. It is therefore believed that the ability of the method of the invention to prevent and treat atherosclerosis is at least partially due to its anti-inflammatory action, and in particular its ability to produce an increase in the TH2 cells and/or a decrease in TH1 cells in the blood of treated subjects, as demonstrated in Example 3. As previously discussed, a relative increase in TH2 cells which secrete anti-inflammatory cytokines, relative to TH1 cells which secrete inflammatory cytokines, would be expected to reduce an autoimmune response.

Although the invention has been described with reference to specific preferred embodiments, it will be appreciated that many variations may be made to the invention without departing from the spirit or scope thereof. All such modifications are intended to be included within the scope of the following claims.

What is claimed is:

1. A method of inhibiting the development of atherosclerotic plaques in a mammalian subject, comprising:
   (a) identifying a subject in need of inhibiting the development of atherosclerotic plaques;
   (b) extracting an aliquot of blood from said subject;
   (c) modifying the extracted blood aliquot extracorporeally by subjecting it to about 0.5–100 µg/ml of ozone gas and ultraviolet radiation at a temperature of from about 0° C. to about 56° C., so as to create in the blood aliquot, in comparison with an equal volume aliquot of the subject's unmodified blood, at least one of the following distinguishing features:
      (i) increased numbers of leukocytes exhibiting a condensed apoptotic-like morphology;
      (ii) a reduction in the number of leukocytes expressing the MHC Class II leukocyte cell surface specific protein HLA-DR;
      (iii) an upregulated expression on leukocytes of the CD-11a cell surface marker;
and re-injecting the blood aliquot so modified into the subject, thereby inhibiting the development of atherosclerotic plaques in said subject.

2. The method of claim 1 wherein the aliquot size is from 0.01–400 ml.

3. The method of claim 2 wherein the aliquot size is from 1–50 ml.

4. The method of claim 1 wherein the ozone gas and ultraviolet radiation are applied to the blood aliquot simultaneously, whilst the blood aliquot is at a temperature of from 37–55° C.

5. The method of claim 1 wherein the ozone is administered as a gas stream in admixture with medical grade oxygen at a rate of from 0.01–2.0 liters per minute (STP), over a period of 0.5–60 minutes.

6. The method of claim 5 wherein the blood aliquot is treated with ozone and ultraviolet radiation at a temperature from 37–43° C., for a period of from 2–5 minutes, the ozone/oxygen mixture being supplied at a rate of from 0.1–1.0 liters per minute, with an ozone content of from 5–50 µg/ml.

7. The method of claim 1 wherein the ultraviolet radiation is supplied from at least one ultraviolet lamp emitting in the C-band wavelength.

8. The method of claim 1 wherein the ultraviolet radiation is obtained from ultraviolet lamps emitting at least about 90% of ultraviolet radiation of a wavelength of about 253.7 nm.

9. The method of claim 1 wherein the extracted blood aliquot is extracorporeally treated so as to create in the subject, a decrease in the ratio of TH1:TH2 cells.

* * * * *